(12) United States Patent
Garcia et al.

(10) Patent No.: US 11,672,648 B2
(45) Date of Patent: Jun. 13, 2023

(54) IMPLANTS WITH SYMMETRIC SHAPE (71) Applicant: ESTABLISHMENT LABS S.A., Alajuela (CR)

(72) Inventors: Camila Garcia, Alajuela (CR); Solange Vindas, Alajuela (CR); Roberto De Mezerville, Alajuela (CR); Juan José Chacón Quirós, Alajuela (CR)

(73) Assignee: Establishment Labs S.A., Alajuela (CR)

( * ) Notice: Subject to any disclaimer, the term of this patent is extended or adjusted under 35 U.S.C. 154(b) by 0 days.

(21) Appl. No.: 17/733,800

(22) Filed: Apr. 29, 2022

(65) Prior Publication Data

US 2022/0257366 A1  Aug. 18, 2022

Related U.S. Application Data

(63) Continuation of application No. 17/262,325, filed as application No. PCT/IB2019/056346 on Jul. 24, 2019.

(60) Provisional application No. 62/703,056, filed on Jul. 25, 2018.

(51) Int. Cl.
*A61F 2/12* (2006.01)

(52) U.S. Cl.
CPC ........ *A61F 2/12* (2013.01); *A61F 2230/0006* (2013.01); *A61F 2230/0008* (2013.01); *A61F 2240/004* (2013.01)

(58) Field of Classification Search
CPC ................ A61F 2/12; A61F 2230/0006; A61F 2230/0008; A61F 2240/004

USPC ......................................................... 623/7–8
See application file for complete search history.

(56) References Cited

U.S. PATENT DOCUMENTS

| | | | |
|---|---|---|---|
| 3,366,975 | A | 2/1968 | Pangman |
| 4,455,691 | A | 6/1984 | Van et al. |
| 4,650,487 | A | 3/1987 | Chaglassian |
| 5,092,882 | A | 3/1992 | Lynn et al. |
| 5,563,211 | A | 10/1996 | Kosal et al. |
| 5,630,844 | A | 5/1997 | Dogan |
| 5,674,285 | A | 10/1997 | Quaid |
| 8,043,373 | B2 | 10/2011 | Schuessler et al. |
| 8,080,598 | B2 | 12/2011 | Irie |
| 8,362,141 | B2 | 1/2013 | Kato et al. |
| 8,580,889 | B2 | 11/2013 | Kato et al. |

(Continued)

FOREIGN PATENT DOCUMENTS

| | | |
|---|---|---|
| BR | 112021001155 A2 | 4/2021 |
| CA | 3106960 | 1/2020 |

(Continued)

OTHER PUBLICATIONS

"International Application Serial No. PCT IB2019 056346, International Search Report dated Mar. 9, 2020", 6 pgs.

(Continued)

*Primary Examiner* — Suzette J Gherbi
(74) *Attorney, Agent, or Firm* — Schwegman Lundberg & Woessner, P.A.

(57) ABSTRACT

Implants having symmetry are described. The implant may comprise a biocompatible material and have at least two planes of symmetry, including symmetry about an equator of the implant. The implant may be a body contouring implant, wherein a posterior side of the implant is symmetric about the equator to an anterior side of the implant.

17 Claims, 5 Drawing Sheets

(56) References Cited

U.S. PATENT DOCUMENTS

| | | |
|---|---|---|
| 8,916,646 B2 | 12/2014 | Kato |
| 9,289,963 B2 | 3/2016 | Yoshida et al. |
| 9,408,692 B2 | 8/2016 | Yu |
| 9,562,158 B2 | 2/2017 | Okada et al. |
| 9,673,516 B2 | 6/2017 | Mejia |
| 9,909,008 B2 | 3/2018 | Kato et al. |
| 9,963,577 B2 | 5/2018 | Park et al. |
| 10,052,191 B2 | 8/2018 | Govrin-yehudian et al. |
| 10,266,693 B2 | 4/2019 | Kihara et al. |
| 11,160,630 B2 * | 11/2021 | Schuessler ............. A61B 90/02 |
| 2003/0205846 A1 | 11/2003 | Bellin et al. |
| 2006/0224239 A1 | 10/2006 | Tiahrt |
| 2007/0135916 A1 * | 6/2007 | Maxwell ................. A61F 2/12 623/8 |
| 2009/0012372 A1 * | 1/2009 | Burnett ................. A61B 5/076 600/300 |
| 2011/0022171 A1 * | 1/2011 | Richter ............... A61L 27/3633 623/8 |
| 2011/0046729 A1 * | 2/2011 | Schuessler ............. A61L 27/26 264/270 |
| 2014/0081398 A1 | 3/2014 | Mejia et al. |
| 2015/0150675 A1 | 6/2015 | Mora et al. |
| 2017/0049549 A1 | 2/2017 | Bayat et al. |
| 2018/0177623 A1 | 6/2018 | Ganz et al. |
| 2019/0040204 A1 | 2/2019 | Beyer et al. |
| 2019/0055420 A1 | 2/2019 | Beyer et al. |
| 2019/0119495 A1 | 4/2019 | Hara et al. |
| 2019/0142574 A1 | 5/2019 | Quirós et al. |
| 2020/0268499 A1 | 8/2020 | Hill et al. |
| 2020/0397554 A1 * | 12/2020 | Van Epps ............ A61F 2/0077 |
| 2021/0093444 A1 * | 4/2021 | Feinberg ................ B29C 41/14 |
| 2021/0186678 A1 * | 6/2021 | Chhaya .................... A61F 2/12 |
| 2021/0259823 A1 * | 8/2021 | Garcia ...................... A61F 2/12 |
| 2022/0151765 A1 * | 5/2022 | Qin ........................... A61F 2/12 |

FOREIGN PATENT DOCUMENTS

| | | |
|---|---|---|
| EP | 2845880 | 3/2015 |
| EP | 3826588 | 6/2021 |
| IL | 280276 | 3/2021 |
| KR | 20210042925 | 4/2021 |
| WO | 2010019292 | 2/2010 |
| WO | 2020021482 | 1/2020 |

OTHER PUBLICATIONS

"International Application Serial No. PCT IB2019 056346, Written Opinion dated Mar. 9, 2020", 11 pgs.

"International Application Serial No. PCT IB2019 056346, International Preliminary Report on Patentability dated Feb. 4, 2021", 13 pgs.

"International Application Serial No. PCT IB2019 056346, Invitation to Pay Additional Fees dated Dec. 17, 2019", 11 pgs.

"U.S. Appl. No. 17/262,325, Preliminary Amendment filed Jan. 22, 2021", 3 pgs.

"European Application Serial No. 19773529.3, Response to Communication pursuant to Rules 161(1) and 162 EPC filed Sep. 14, 2021", 13 pgs.

"Israel Application Serial No. 280276, Notice according to regulation 36 dated Aug. 29, 2021", w o English translation, 2 pgs.

"Israel Application Serial No. 280276, Response filed Feb. 28, 2022 to Notice according to regulation 36 dated Aug. 29, 2021", 1 pg.

"European Application Serial No. 22179756.6, Extended European Search Report dated Sep. 29, 2022", 9 pgs.

* cited by examiner

IMPLANTS WITH SYMMETRIC SHAPE

CROSS-REFERENCE TO RELATED APPLICATION(S)

This application claims benefit of priority under 35 U.S.C. § 119 to U.S. Provisional Application No. 62/703,056, filed on Jul. 25, 2018, the entirety of which is incorporated herein by reference.

TECHNICAL FIELD

Embodiments of the present disclosure relate generally to medical implants and related methods of manufacturing and use thereof.

BACKGROUND

Many implants currently available in the market are vulnerable to misplacement during and/or after implantation in a patient. For example, breast implants, particularly round breast implants, can flip in some circumstances, such that the posterior, flat surface faces the skin rather than the chest wall. This susceptibility to misplacement can complicate the implantation procedure. Care must be taken to maintain the proper orientation when introducing an implant through small incision sites and/or tortuous anatomy to avoid irregular positioning at the implantation site. Implant flipping can occur after implantation, wherein the patient could notice abnormal appearance, such as a lump in the breast. In addition to aesthetic concerns, this could cause insecurity on the part of the patient that something went wrong with the surgery or there is another potentially serious medical issue.

SUMMARY OF THE DISCLOSURE

Implants and methods of manufacture and use thereof are described. The present disclosure includes a medical implant comprising a biocompatible material and having at least two planes of symmetry, optionally three planes of symmetry, wherein one of the at least two planes of symmetry corresponds to an equator of the implant. The implant may be a body contouring implant, such as a breast implant or a gluteal implant, a tissue expander, a sizer, or a tissue dissector, for example, wherein the posterior side of the implant is symmetric about the equator to the anterior side of the implant. According to some aspects herein, the implant may have a round shape, an oval shape, or a teardrop shape.

The implants herein may include a shell and a filler, optionally wherein the shell has a patch affixed thereto. For example, the implant may have a first side and a second side symmetric about the equator, the implant including a patch located between an apex of the first side and the equator, or between an apex of the second side and the equator, optionally wherein the patch is located less than or equal to 20 mm from the equator, less than or equal to 18.9 mm from the equator, less than or equal to 15 mm from the equator, less than or equal to 10 mm from the equator, less than or equal to 7.5 mm from the equator, less than or equal to 5.5 mm from the equator, less than or equal to 5 mm from the equator, optionally wherein at least a portion of the patch is located at the equator. In some examples, the implant includes a patch having a diameter less than or equal to 30 mm, such as less than or equal to 27 mm, less than or equal to 25 mm, less than or equal to 20 mm, or less than or equal to 19 mm. Additionally or alternatively, the implant may include a label imprinted thereon for identifying the implant, optionally wherein the label includes a name and/or location of a manufacturer, an implant model number, one or more size dimensions, a date of manufacture, or a combination thereof. For example, the label may be printed on the patch. The implants herein may include a transponder, optionally disposed in a filler proximate an apex (e.g., posterior apex or anterior apex) of the implant.

In some examples, the implant is a breast implant comprising a filler in the form of a fluid, e.g., a gel filler, having a viscosity or penetration value suitable for simulating movement of natural breast tissue. For example, the filler may comprise a gel having a penetration value (1/10 mm) ranging from about 10 to about 60.

At least a portion of an outer surface, or the entire outer surface, of the implant may be texturized with surface features on the order of nanometers to micrometers. Optionally the implant comprises a shell that includes a patch, the outer surface of the patch being texturized with surface features on the order of nanometers to micrometers.

The present disclosure further includes use of the implants herein, including any of the implant described above or elsewhere herein, in a minimally-invasive implantation procedure.

The present disclosure further includes a method of manufacturing such implants. For example, the methods herein include manufacturing an implant comprising a biocompatible material, wherein the implant comprises a shell that includes exactly one low diffusion barrier the forms an outermost surface of the shell. In some examples, preparing a shell of the implant may comprise applying a first silicone dispersion to a surface of a mold to form at least one first layer of the shell; and applying a second silicone dispersion to the at least one first layer to form at least one second layer; wherein the first silicone dispersion or the second silicone dispersion comprises a colored silicone elastomer that includes a dye or a pigment, and the other of the first silicone dispersion or the second silicone dispersion does not include a dye or a pigment. The second silicone dispersion may comprise, for example, the colored silicone elastomer, the at least one second layer being a low diffusion barrier layer, optionally wherein the second silicone dispersion comprises from about 0.01% to about 0.05% by weight of the blue silicone elastomer, with respect to the total weight of the second silicone dispersion. The colored silicone elastomer may be blue, green, yellow, pink, orange, or purple, for example. According to some aspects herein, the method includes applying 2, 3, 4, or 5 first layers, and then applying only one second layer over the first layers. Further, the methods of manufacturing may include applying exactly 6 layers, the shell optionally having a total thickness ranging from about 0.010 inches to about 0.040 inches before and/or after curing the shell.

The method may further comprise curing the shell, optionally wherein the curing is performed at a temperature ranging from about 115.0° C. to about 135.0° C. Additionally or alternatively, the method may comprise removing the shell from the mold and inverting the shell, optionally wherein a surface of the mold is texturized with surface features on the order of nanometers to micrometers, such that an outermost surface of the shell, when inverted, is texturized. Further, for example, the method may comprise introducing a gel into a cavity of the shell, optionally wherein the gel has a penetration value (1/10 mm) ranging from 10 to 60. The method may further comprise applying a patch to a hole of the shell and sealing the patch to the shell, optionally wherein the patch includes a transponder incorporated between layers of the shell or patch or attached to an inner surface of the shell or patch. In some examples, the transponder is not attached to the shell or the patch. The method may further comprise introducing a transponder into a cavity of the shell, e.g., before or after introducing a filler into the cavity. Thus, for example, the transponder may be (a) disposed within the gel and unattached to an inner surface of the shell, or (b) attached to an inner surface of the shell or incorporated into a portion of the shell. The method may further comprise heating the implant to cure a gel disposed inside a cavity of the shell, wherein the implant is placed in a substrate, such as in a cavity of a substrate, during the heating to maintain a symmetrical shape of the implant.

The present disclosure further includes molds for preparing implants described above and elsewhere herein. For example, the mold may be or comprise a mandrel comprising a head and a handle, the head having a symmetric shape having at least two planes of symmetry corresponding to the at least two planes of symmetry of the implant, optionally wherein the head has a textured surface. The head of the mandrel may be centered or offset relative to the handle.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "about" and "generally," are used to indicate a possible variation of ±5% of a stated or understood value.

As used herein, the term "posterior" refers to the back of a patient, and the term "anterior" refers to the front of a patient. Thus, for example, the side of a breast implant closest to the skin is the anterior side, while the side of a gluteal implant closest to the skin is the posterior side.

The present disclosure includes implants having a shape that is symmetric, e.g., having at least one plane of symmetry. The implant may be any type of implant suitable for implantation into the body, including, but not limited to, aesthetic implants such as breast, gluteal, and calf implants. In this way, the implant may be inserted into a patient such that either side of the implant may face in the posterior direction or the anterior direction.

Symmetrical characteristics of the implant may allow for a similar or the same projection at the apex of the posterior side of the implant as the anterior side. The implant may avoid or eliminate issues related to the potential flipping of the implant after surgery and/or during the implantation process. Further, having a symmetrical shape may provide benefits in minimally-invasive implantation procedures. For example, the ability to introduce the implant in different orientations may allow for a smaller-sized incision. The implants herein may be implanted into a patient in a hybrid-type procedure, e.g., as disclosed in PCT Application PCT/US19/38536, which claims the priority from U.S. Provisional Application No. 62/688,778 filed on Jun. 22, 2018, by introducing a filler material such as autologous fat together with the implant during the implantation procedure.

In some examples herein, the implant is a body contouring implant. For example, the body contouring implant may have a plane of symmetry along its equator, corresponding to an xy plane (the length dimension x extending in the direction from top to bottom of the implant, and the width dimension y extending in the direction from left to right of the implant). Such implants may have a generally round, oval, or teardrop shape.

Figure 1A:
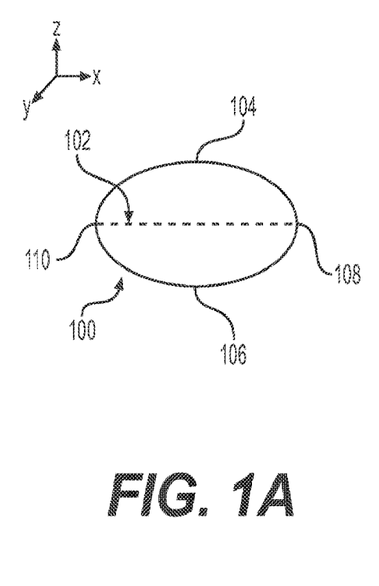
FIGS. 1A-IC show cross-sections of an exemplary implant, in accordance with embodiments of the present disclosure.
Figure 1B:
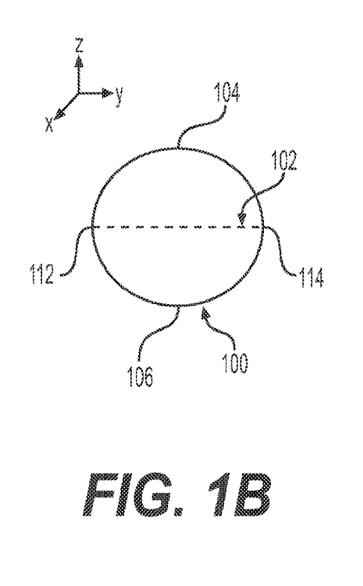
Figure 1C:
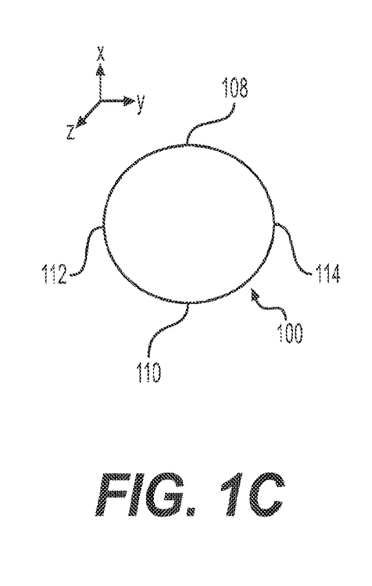

FIGS. 1A, 1B, and 1C show an exemplary implant 100 having a round or oval shape, the implant 100 having symmetry in accordance with one or more embodiments of the present disclosure. Such implants include, for example, body contouring implants such as breast implants, pectoral implants, gluteal implants, as well as other types of implants associated with aesthetic and/or reconstructive procedures, such as sizers (e.g., breast sizers or any device that is configured to define the final size of the implant), tissue expanders (e.g., breast expander or any temporary implant used for reconstruction s), and tissue dissectors (e.g., breast dissectors or any device that is configured to separate the tissue or muscle in order to create the space to place a permanent implant). FIG. 1A shows a cross-sectional view of the implant 100 in the xz plane, FIG. 1B shows a cross-sectional view of the implant 100 in the yz plane, and FIG. 1C shows a cross-sectional view of the implant 100 in the xy plane. The xy plane corresponds to a plane generally parallel to the chest wall of a patient when the implant is implanted, referred to as the equator 102. Thus, FIG. 1C depicts a cross-section of the implant 100 along the equator 102. The upper and lower portions of the implant 100 are separated by the yz plane, and the left and right portions of the implant 100 are separated by the xz plane.

As shown in FIGS. 1A and 1B, the implant 100 has symmetry about the xy plane (above and below the equator 102), such that the anterior side and posterior side of the implant are symmetric. That is, a first side 104 is symmetric to a second side 106 about the equator 102, such that the first side 104 may correspond to the posterior side and the second side 104 may correspond to the anterior side, or vice versa, when implanted in a patient. As shown in FIGS. 1A and 1C, the implant 100 also has symmetry about the yz plane, such that the upper and lower sides of the implant 100 are symmetric to each other (see upper and lower sides 108, 110). As shown in FIGS. 1B and 1C, the implant 100 further has symmetry about the xz plane, such that the left and right sides of the implant 100 are symmetric to each other (see left and right sides 112, 114). Thus, the implant 100 has at least three planes of symmetry.

Figure 2A:
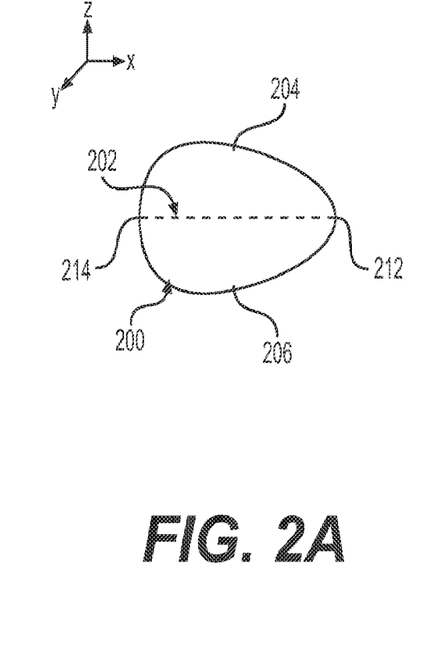
FIGS. 2A-2C show cross-sections of another exemplary implant, in accordance with embodiments of the present disclosure.
Figure 2B:
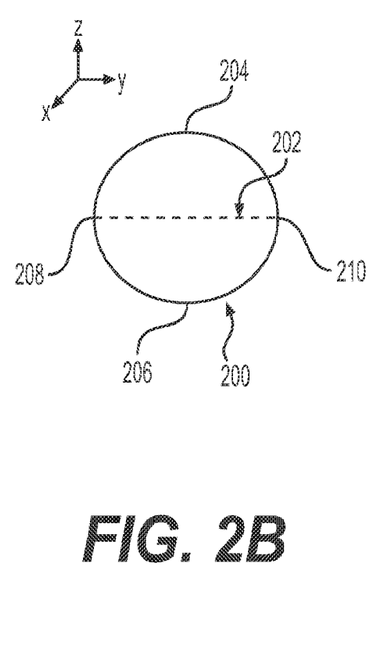
Figure 2C:
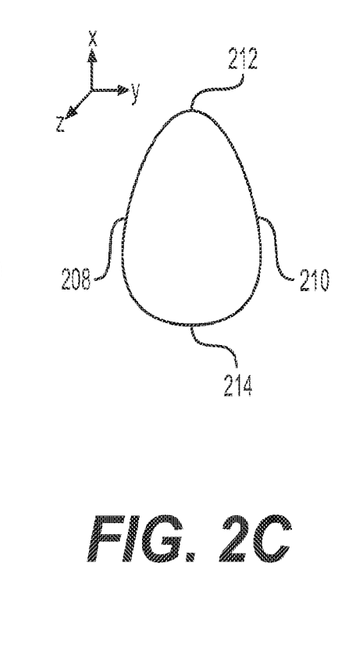

Other exemplary implants may have at least one plane of symmetry, but fewer than three planes of symmetry. For example, the implant may have a teardrop shape. Such implants include, for example, body contouring implants such as breast implants, pectoral implants, gluteal implants, and facial implants. FIGS. 2A, 2B, and 2C show cross-sectional views of an exemplary implant 200 that has a teardrop shape, in accordance with one or more embodiments of the present disclosure. FIG. 2A shows a cross-sectional view of the implant 200 in the xz plane, and FIG. 2B shows a cross-sectional view of the implant 200 in the yz plane, wherein the equator 202 lies along the xy plane. FIG. 2C shows a cross-sectional view of the implant 200 in the xy plane, along the equator 202. The implant 200 has symmetry about the xy plane (above and below the equator 202 in FIGS. 2A and 2B, corresponding to the anterior and posterior sides 204, 206 when implanted), and about the xz plane (see left and right sides 208, 210 in FIGS. 2B and 2C). The implant 200 does not have symmetry about the yz plane (see upper and lower sides 212, 214 in FIG. 2A and FIG. 2C). In this example, the implant 200 has two planes of symmetry. Additional examples of body contouring implants and other types of implants are included herein.

One or more surfaces of the implant may have a surface texture (e.g., microtexture or nanotexture) to promote biocompatibility. For example, the implant may have a surface texture as disclosed in WO 2017/196973, WO 2015/121686, and/or WO 2017/093528, each incorporated by reference herein. For example, the surface texture may include uniform surface features on the order of nanometers to micrometers.

According to some examples herein, the implant may comprise a shell and a filler (e.g., a fluid such as a gel or a liquid) inside a cavity formed by the shell. The shell and the filler may each comprise a biocompatible material, such as silicone. Any of the materials and/or features discussed in U.S. Pat. No. 9,901,438, US 2015/0150675, and/or WO 2017/196973, each incorporated by reference herein, may be used for the implants herein.

The shell of the implant may comprise a biocompatible material, e.g., formed as a plurality of layers. An outer and/or inner surface of the shell may have a surface texture, e.g., as disclosed in WO 2017/196973, WO 2015/121686, and/or WO 2017/093528, each incorporated by reference herein.

According to some examples herein, the implant may comprise a shell having a total thickness ranging from about 0.010 inches to about 0.040 inches, such as from about 0.013 inches to about 0.040 inches, from about 0.010 inches to about 0.020 inches, from about 0.012 inches to about 0.015 inches, from about 0.010 inches to about 0.015 inches, from about 0.013 inches to about 0.025 inches, from about 0.015 inches to about 0.030 inches, or from about 0.020 inches to about 0.040 inches. The shell may comprise at least one layer or a plurality of layers, e.g., having a total thickness of at least 0.01 inches, at least 0.012 inches, at least 0.015 inches, at least 0.02 inches, at least 0.025 inches, at least 0.03 inches, at least 0.035 inches, or at least 0.04 inches. Elongation and ultimate break force of the shell can be measured according to Non-active surgical implants—Mammary implants—Particular requirements ISO 14607: 2018.

According to some aspects of the present disclosure, the implant shell may comprise a plurality of layers. For example, the shell may comprise from 1 to 15 layers, from 2 to 8 layers, from 3 to 7 layers, from 4 to 15 layers, from 6 to 8 layers, from 10 to 13 layers, or from 12 layers to 15 layers. For example, the shell may comprise at least 1, 2, 3, 4, 5, 6, or 7 or more layers, e.g., 2 to 15 layers, 3 to 7 layers, 1 to 5 layers, or 4 to 8 layers. In some cases, one or more of the layers, or all of the layers, may comprise silicone. For example, one or more of the layers, or all of the layers, may comprise polydimethylsiloxane.

According to some examples herein, the shell comprises at least two different types of layers, e.g., having different chemical compositions. In some examples, the number of each of the two types of layers may be 1, 2, or 3 layers. Each layer may have the same thickness, or one or more layers may have a thickness different from one or more other layers of the shell. The shell may include at least two layers including a colored layer, e.g., a low diffusion barrier layer. One or more low diffusion barrier layers may be useful, for example, for implants intended to remain in the body for a relatively long period of time, e.g., to inhibit leakage of materials within the implant into the body. For example body contouring implants such as breast implant with a filler may include one or more low diffusion barrier layers. In some cases, e.g., for implants that do not include a filler and/or implants intended to be placed within the body for a relatively shorter amount of time, the implant does not include a low diffusion barrier layer. For example, such implant may include a single type of layer, e.g., one or more layers having the same chemical composition. Exemplary implants that do not comprise a barrier layer may include, for example, sizers, tissue expanders, and tissue dissectors.

When present, the barrier layer(s) may have any desired color, such as blue, green, yellow, pink, orange, purple, or other colors. In some cases, the barrier layer has the same color as other layers (including non-barrier layers) present in the shell. The low diffusion barrier layer(s) may have a chemical composition different from the chemical composition of other layers. For example, the barrier layer(s) may comprise a silicone elastomer having a polysiloxane backbone and substituted or pendant functional groups that inhibit permeation of silicone through the layer. The silicone elastomer may comprise polydimethylsiloxane. Exemplary functional groups include, but are not limited to, phenyl groups and fluorine groups. For example, the barrier layer(s) may comprise silicone substituted with one or more diphenyl groups, methylphenyl groups, trifluorpropyl groups, and combinations thereof.

Figure 4:
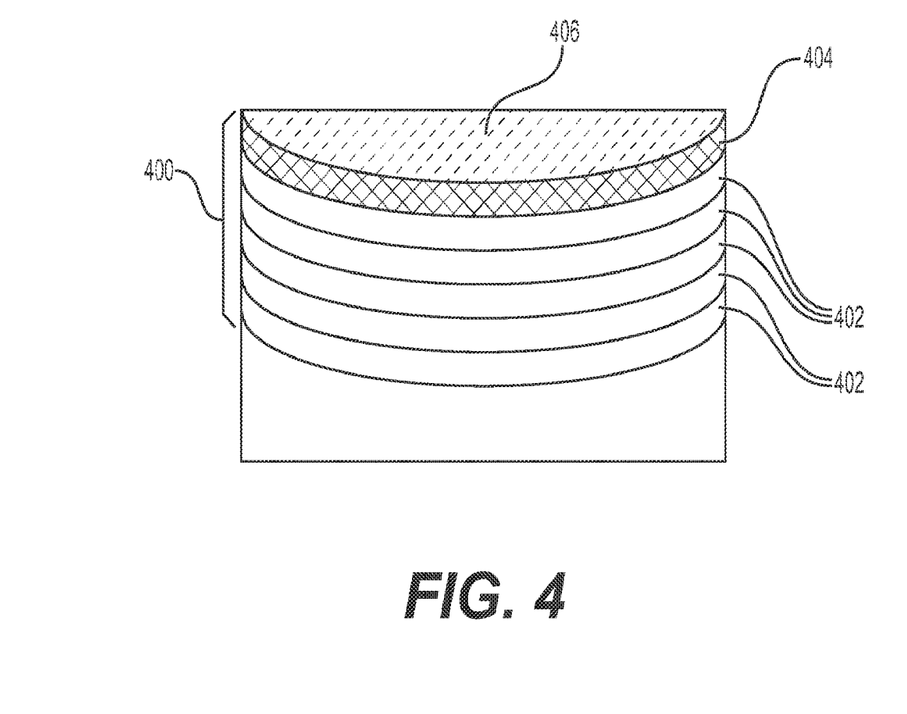
FIG. 4 shows an exemplary configuration of layers of an implant shell, in accordance with one or more embodiments of the present disclosure.

FIG. 4 shows an exemplary configuration of shell layers, in accordance with some aspects of the present disclosure. As illustrated, the shell 400 comprises a plurality of layers, including one or two types of layers. For example, the shell may comprise one or more first layers 402 and one or more second layers 404. In this example, the shell 400 is depicted with five first layers 402 and one second layer 404, however, the shell may include more or fewer than five first layers and/or more than one second layer 404. FIG. 4 shows the second layer 404 as the innermost layer of the shell, (e.g., in contact with a filler 406 enclosed within the shell 400). In other examples, the shell may include two or more second layers positioned as the outermost layer(s) of the shell or between two first layers 402. Further, the shell may include two or more second layers 404 with one or more first layers 402 between the second layers 404.

The second layer(s) 404 may have a different chemical composition than the first layer(s) 402. For example, the second layer(s) may be low diffusion barrier layer(s), which may minimize or prevent diffusion of the filler though the wall of the shell (e.g., to minimize or prevent filler from leaking outside the implant). As depicted in FIG. 4, the low diffusion barrier layer(s) may form the innermost layer of the shell, next to the filler 406, such as saline solution or a gel (e.g., silicone gel). The layers of the shell may lie in direct contact with each other, such that the outer and/or inner surface of one layer is entirely covered by an adjacent layer.

The implant may include a patch, e.g., affixed to the shell. For example, the shell may be prepared by a molding process that leaves an opening in the shell, wherein the patch is affixed to the shell to cover the opening. In an exemplary process, a mandrel may be used to prepare a body contouring implant, such as a breast implant. The patch may comprise the same or different material(s) as the shell. The implants herein may include a patch having any of the features of patches disclosed in U.S. Pat. No. 9,901,438 and/or WO 2017/196973, each incorporated by reference herein.

Figure 3A:
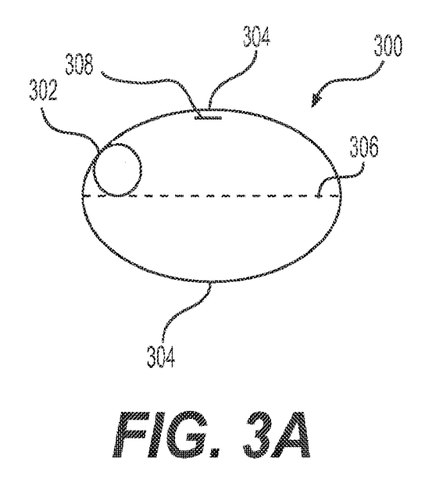
FIGS. 3A-3C show side views of implants with different shall configurations, in accordance with embodiments of the present disclosure.
Figure 3B:
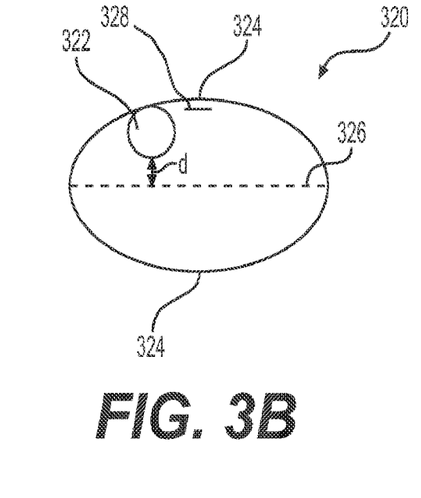
Figure 3C:
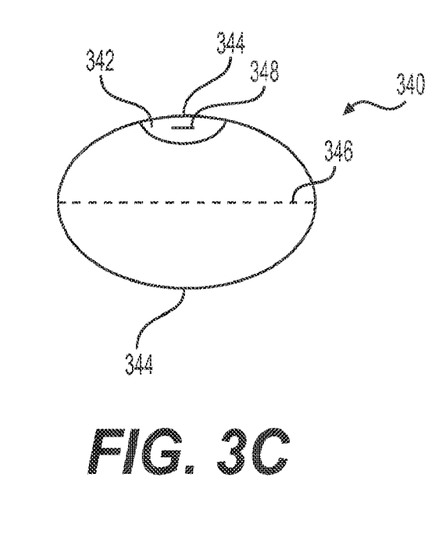

The patch may be located at any suitable position along the shell. FIGS. 3A, 3B, and 3C illustrate, in side view, examples of implants 300, 320, 340 with patches 302, 322, 342 placed at different locations, in accordance with the present disclosure. Each implant 300, 320, 340 is symmetric about the xy plane about its equator 306, 326, 346, respectively, each implant 300, 320, 340 having two apices 304, 324, 344 opposite each other, corresponding to a posterior side apex and an anterior side apex. FIG. 3C shows an implant 340 having a patch 342 at one of the two apices 344.

According to some aspects of the present disclosure, the implant may include a patch located in a position other than an apex. For example, FIGS. 3A and 3B show implants 300, 320 having respective patches 302, 322 located between an apex 304, 324 and the equator 306, 326, of each implant. The shortest distance between the patch and the equator (e.g., a shortest distance d in FIG. 3B) may be greater than zero and/or less than about 25 mm, such as a distance of at least 1 mm, at least 2 mm, at least 5.5 mm, at least 7 mm, at least 9 mm, at least 10 mm, at least 13 mm, at least 15 mm, at least 18 mm, at least 19 mm, at least 20 mm, at least 22 mm, or at least 24 mm. Additionally or alternatively, the shortest distance between the patch and the equator may be greater than zero and less than or equal to 30 mm, less than or equal to 25 mm, less than or equal to 20 mm, less than or equal to 19 mm, less than or equal to 18 mm, less than or equal to 15 mm, less than or equal to 13 mm, less than or equal to 10 mm, less than or equal to 9 mm, less than or equal to 7 mm, less than or equal to 5 mm, less than or equal to 3 mm, less than or equal to 2 mm, or less than or equal to 1 mm. For example, the shortest distance between the patch and the equator may range from about 1 mm to about 30 mm, about 5 mm to about 25 mm, about 10 mm to about 20 mm, about 1 mm to about 5 mm, about 3 mm to about 7 mm, about 5 mm to about 10 mm, about 2 mm to about 12 mm, about 7 mm to about 15 mm, about 3 mm to about 6 mm, about 8 mm to about 12 mm, about 7 mm to about 9 mm, about 10 mm to about 15 mm, or about 17 mm to about 23 mm, e.g., as a shortest distance of about 3 mm, about 3.5 mm, about 4 mm, about 4.5 mm, about 5 mm, about 5.5 mm, about 6 mm, about 6.5 mm, or about 7 mm. In some examples, at least a portion of the patch is located at the equator. For example, the center of the patch may lie along or proximate the equator, e.g., located at an angle of about 90 degrees relative to the posterior side apex and/or anterior side apex.

The shape of the patch may be generally circular, elliptical, or polygonal (e.g., triangular, square, rectangular, pentagonal, etc.). The width and/or length of the patch (diameter in the case of a circular shape) may range from about 10 mm to about 40 mm. For example, the patch may have a length, width, and/or diameter ranging from about 10 mm to about 35 mm, about 15 mm to about 25 mm, about 10 mm to about 15 mm, about 12 mm to about 18 mm, about 24 mm to about 28 mm, about 20 mm to about 25 mm, or about 25 mm to about 35 mm.

According to some aspects of the present disclosure, the implant may include text (e.g., letters, words, numbers, signs, and/or symbols) imprinted thereon. For example, the implant may include one or more labels with identifying information, such as the name and/or location of the manufacturer, the model number, size dimensions (e.g., diameter, volume, projection, etc.), the date of manufacture, and/or other identifying information. The label(s) may be located on or incorporated into the outer surface of the implant. In the case of an implant with a shell, such as a breast implant or other body contouring implant, one or more labels may be imprinted onto or into a portion of the shell or a component coupled to the shell.

For example, the implant may include a patch as discussed above, wherein the patch includes text imprinted thereon useful for identifying the implant. In some cases, the text may be imprinted into the outer surface of the patch, such that the text is raised relative to the remainder of the outer surface of the implant. Additionally or alternatively, the printing surface may be reversed, wherein the text is recessed relative to the remainder of the outer surface of the implant and/or imprinted into the inner surface of the patch that contacts the filler of the implant. Having a reversed printing surface may help to promote symmetry of the implant and avoid an irregular outer surface that could lead to adverse reactions upon contact with breast tissue once implanted. In some examples, the outer surface of the implant may include a label that does not have raised text, the printing surface being reversed. Further, for example, a portion of the outer surface of the implant other than the patch may include a label.

The outer surface of the patch may be texturized, e.g., with the same or different surface texture as adjacent surfaces of the surrounding shell. For example, the patch may have any of the surface characteristics disclosed in WO 2017/196973, WO 2015/121686, and/or WO 2017/093528, each incorporated by reference herein. When the patch has the same or substantially the same surface texture as the remainder of the shell, the implant may have a homologous surface texture. The filler of the implants herein may comprise a fluid, such as a gel, a liquid, or a gas. Exemplary gels include, but are not limited to, silicone and other biocompatible polymers. Exemplary liquids include, but are not limited to, saline solution. Exemplary gases include, but are not limited to, air. Additionally or alternatively, the filler may comprise a solid material, such as a biocompatible scaffold, optionally a biocompatible polymer. According to some aspects of the present disclosure, the filler may comprise a gel having a viscosity suitable for simulating natural tissue, e.g., the gel being responsive to gravity such that the maximum point of projection of the implant changes as the patient moves from a standing position to a supine position. Exemplary gels suitable for fillers herein may have a gel penetration value (1/10 mm) ranging from about 10 to about 60, for example, the implants herein may comprise a gel filler having a penetration value (1/10 mm) ranging from about 10 to about 30, from about 20 to about 35, from about 50 to about 60, from about 35 to about 55, from about 15 to about 30, or from about 10 to about 20. The penetration value is a factor that measures the firmness of a colloid, such as a silicone gel. The penetration value may be measured according to standard ISO 14607:2018. The combination of shell elasticity and gel viscosity may provide certain benefits for implantation in a minimally-invasive procedure, e.g., in an incision of about 2 cm or smaller.

The implants herein may include information useful in identifying and/or characterizing the implant. In some aspects of the present disclosure, the implant may include an orientation mark (e.g., a radiopaque marker), a traceability device such as a radio-frequency identification (RFID) device and/or one or more sensors. For example, the implant may include a unique device identifier (UDI), optionally coupled to, or otherwise incorporated into, a portion of the implant shell and/or patch. The UDI may include, for example, a transponder. In cases in which the implant shell includes a patch, the transponder may be located proximate the patch (e.g., positioned proximate an inner surface of the patch) or may be located in an area of the implant different from the patch (including, e.g., proximate an inner surface of the shell spaced apart from the patch).

FIGS. 3A-3C illustrate exemplary transponders 308, 328, 348 (also referred to as micro-transponders) associated with the respective implants 300, 320, 340. The transponder may be in any area at or proximate an apex (e.g., posterior apex or anterior apex) and/or may be proximate the patch. For example, FIGS. 3A and 3B illustrate examples wherein the transponders 308, 328 are disposed within filler at or proximate the posterior apex or anterior apex, while the patches 302, 322 are located between the posterior or anterior apex and the equator, while FIG. 3C illustrates an example wherein the transponder 348 and the patch 342 are both at or proximate the posterior or anterior apex. In some examples, the transponder may be disposed within the filler near the patch but not attached to or otherwise coupled to the patch. In other examples, the transponder may be coupled to an inner surface of the shell or patch, or disposed between two layers of the shell or patch, for example, if desired to have the transponder located at a position other than the posterior or anterior apex.

The transponder may have RFID capability, for post-implantation device recognition and traceability. For example, information stored in the transponder may be readable by an external device, such as an RFID reader. Any of the transponders and/or readers disclosed in U.S. Pat. Nos. 9,673,516 and/or 10,176,412, each incorporated by reference herein, may be included in the implants of the present disclosure. Exemplary transponders may comprise, for example, an antenna assembly comprising ferromagnetic and/or non-ferromagnetic materials.

In at least one example, the implant comprises a transponder that does not include ferromagnetic materials. For example, the transponder may comprise one or more plastics, such as poly-ether-ether-ketone (PEEK), a ceramic, silica, or other non-ferromagnetic material(s). Accordingly, the implant may be compatible with diagnostic imaging procedures, such as magnetic resonance imaging (MRI). The antenna assembly of the transponder may comprise a conductive, non-ferromagnetic material, such as copper or aluminum, among other suitable non-ferromagnetic metals. Such metals may be in the form of a metal wire, optionally an enameled wire, e.g., configured into an coil wound around a non-ferromagnetic core.

As mentioned above, the implant shell may be prepared by dip molding. For example, each layer may be formed by dipping a mold (e.g., a mandrel) into a dispersion, e.g., comprising a silicone material, and waiting a period of time sufficient for the solvent to volatilize (devolatilization time), such that the dispersion forms a layer. The mold may have a symmetric shape in order to produce an implant shell with the desired symmetry as discussed above. For example, a mandrel may have a head that is generally round, oval, or teardrop shape, the mandrel having a handle or stem coupled to or protruding from the head for gripping during the dip-molding process. When it is desired for the patch to be located at an apex (e.g., anterior apex or posterior apex), the head of the mandrel may be centered relative to the handle so as to leave an opening in the shell at the apex. When it is desired for the patch to be located in a position other than an apex (e.g., between the equator and the anterior apex or posterior apex), the head of the mandrel may be offset relative to the handle so as to leave an opening between the apex and the equator. That is, a longitudinal axis of the handle is offset from a z-axis of the head of the mandrel that connects the two apices of the head.

Exemplary dispersions suitable for forming silicone layers for an implant shell according to the present disclosure are discussed below. The dispersions for preparing the first layer(s) 402 and the second layer(s) 404, and/or additional layers may be a silicone dispersion, e.g., prepared from two components.

For example, to prepare the first layer(s) 402, a first dispersion may be prepared from a two-part curable system (part A and part B), e.g., using a platinum catalyst. Each component/part may comprise a dispersion of siloxanes and silicones. For example, part A may comprise a high strength silicone dispersion of siloxanes and silicones, dimethyl, vinyl group-terminated and silanamine, 1,1,1-trimethyl-N (trimethylsilyl)-, hydrolysis products with silica. Part B may comprise a high strength silicone dispersion of siloxanes and silicones, dimethyl, vinyl group-terminated and siloxanes and silicones, dimethyl, methyl hydrogen.

Further, for example, to prepare the second layer(s) 404 (e.g., low diffusion barrier layer(s)), a second dispersion may be prepared also from a two-part curable system (part A and part B), e.g., using a platinum catalyst, optionally with a pigment or dye (e.g., in the form of a colored liquid silicone elastomer) to result in a colored dispersion. Incorporating a pigment or dye may assist in quality control to visually confirm that the low diffusion barrier layer(s) are present and continuous throughout the shell. Part A may comprise a silicone dispersion comprising xylenes (o-, m-, p-isomers) and silanamine, 1,1,1-trimethyl-N(trimethylsilyl)-, hydrolysis products with silica. Part B may comprise a silicone dispersion comprising xylenes (o-, m-, p-isomers), silanamine, 1,1,1-trimethyl-N(trimethylsilyl)-, hydrolysis products with silica, siloxanes and silicones, dimethyl, methyl hydrogen and cyclohexanol, 1-ethynyl-. The colored dispersion may comprise a silicone elastomer having any desired color, such as blue, green, yellow, pink, orange, purple, etc. For example, a blue second layer 404 may be prepared from a liquid silicone elastomer comprising pigment blue 15:2, phthalo blue (NC α-Form), phthalocyanine blue bs, or (29H,31H-phthalocyaninato(2-)—N29,N30,N31, N32)copper. Other biocompatible dyes and/or pigments compatible with silicone dispersions may be used in the shell layer(s), e.g., one or more second layers 404, for the implants herein.

For either of the first dispersion used to prepare first layer(s) 402 and/or the second dispersion used to prepare the second layer(s) 404, parts A and B may be combined in a weight ratio ranging from about 1:2 to about 2:1, such as in a ratio of about 1:1. In some embodiments, for each layer, parts A and B may be combined in a weight ratio at least about 1:10, 1:9, 1:8, 1:7, 1:6, 1:5, 1:4, 1:3, 1:2, 1:1, or more. In some embodiments, for each layer of the implant shell, parts A and B may be combined in a weight ratio at most about 10:1, 9:1, 8:1, 7:1, 6:1, 5:1, 4:1, 3:1, 2:1, 1:1, or less. An organic solvent, such as xylene, may be added to achieve a desired viscosity or range of viscosity.

For the dispersion used to prepare the second layer(s) 404 (e.g., low diffusion barrier layer(s)), the amount of the colored liquid silicone elastomer (containing the pigment or dye) may range from about 0.01% to about 0.05% by weight, such as from about 0.01% to about 0.05% by weight, with respect to the weight of the dispersion formed from mixing part A and part B. For example, the second dispersion used to prepare low diffusion barrier layers 404 may comprise part A and part B in a weight ratio of about 1:1, and from 0.01% to about 0.05% by weight of pigment blue 15-2, phthalo blue (NC α-Form), phthalocyanine blue bs, or (29H,31H-phthalocyaninato(2-)—N29,N30,N31,N32)copper. The amount of the colored liquid silicone elastomer may be at least 0.01%, at least 0.05%, at least 0.1%, at least 0.15%, at least 0.2%, at least 0.3%, at least 0.4%, or at least 0.5% by weight with respect to the weight of the dispersion formed from mixing part A and part B. Additionally or alternatively, the amount of the colored liquid silicone elastomer may be less than or equal to 0.5%, less than or equal to 0.4%, less than or equal to 0.3%, less than or equal to 0.2%, less than or equal to 0.1%, less than or equal to 0.05%, less than or equal to 0.03%, or less than or equal to 0.01% by weight with respect to the weight of the dispersion formed from mixing part A and part B.

Exemplary methods of manufacturing implant shells according to the present disclosure may comprise one or more steps of testing dispersions, mixing the dispersions, molding a shell (dip-molding), curing the shell, removing the shell from the mold, and/or performing quality inspections. Methods of manufacturing according to the present disclosure may comprise some, but not all, of the steps discussed above. The methods herein may be used to manufacture a plurality of shells simultaneously.

In an exemplary method, a silicone dispersion may be prepared for each type of layer 402, 404 to be included in the implant shell. Part A and part B for each type of dispersion may be mixed in a suitable ratio as discussed above, such as a 1:1 ratio, a 1:2 ratio, a 2:1 ratio, or a 1:1.5 ratio. A solvent may be added to obtain a desired viscosity or a range of viscosities, as described herein. For the second layer(s) 404 (e.g., low diffusion barrier layer(s)), a pigment, optionally in the form of a colored liquid silicone elastomer, may be added once part A and part B have been combined. The viscosity in combination with the solvent devolatilization time may allow for the shell substantially free of, or having no cosmetic defects, and within a thickness or a range of thickness.

Molds may be selected according to the type of implant desired. For example, the molds suitable for use herein may have a symmetric shape, having at least one plane of symmetry. Then, the mold may be introduced into the selected dispersion (e.g., a first dispersion for preparing a first layer 402) to coat the mold for a period of time equal to the devolatilization time, and then the coated mold may be re-introduced into the same dispersion (e.g., the first dispersion to prepare another first layer 402) or a different dispersion (e.g., a second dispersion for preparing a second layer 404) to build another layer in the shell. Dip molding may be repeated until the desired number of layers and total shell thickness are achieved. Exemplary devolatilization times may range from about 10 minutes to about 45 minutes, such as from about 15 minutes to about 35 minutes, from about 20 minutes to about 40 minutes, from about 10 minutes to about 20 minutes, or from about 35 minutes to about 45 minutes. The devolatilization time may be at least 5 minutes, 10 minutes, 15 minutes, 20 minutes, 25 minutes, 30 minutes, 35 minutes, 40 minutes, 45 minutes, or longer. In some embodiments, the devolatilization time may be at most 45 minutes, 40 minutes, 35 minutes, 30 minutes, 25 minutes, 20 minutes, 15 minutes, 10 minutes, 5 minutes, or shorter.

Table 1 below illustrates several exemplary 6-layer shells that include two different types of layers, e.g., one or more first layers 402 and one or more second layers 404, wherein the second layer(s) 404 have a different chemical composition than the first layer(s) 402. The second layer(s) 404 optionally may be low diffusion barrier layer(s), or may be non-barrier layers having a different chemical composition than other non-barrier layer(s). In Table 1, implant shell A corresponds to the example shown in FIG. 4. For example, to prepare implant shell A, wherein a mold (e.g., mandrel for a body contouring implant) may be dipped into a first dispersion to form a layer 402 next to the mold surface. After the devolatilization time, the coated mold may be again dipped into the first dispersion to form an additional layer 402; and after the devolatilization time, the coated mold may again dipped into the first dispersion to form an additional layer 402, and so on, until the coated mold is dipped into a second dispersion to form a second layer 402, as a low diffusion barrier layer. A person of ordinary skill in the art will recognize that the configurations in Table 1 are exemplary only, and fewer or more than 6 layers may be prepared, and layers may be provided in a different order.

TABLE 1

| | Type of Layer | | |
|---|---|---|---|
| | A | B | C |
| layer 1 (next to mold surface) | 402 | 404 | 402 |
| layer 2 | 402 | 402 | 402 |
| layer 3 | 402 | 402 | 404 |
| layer 4 | 402 | 402 | 404 |
| layer 5 | 402 | 402 | 402 |
| layer 6 (farthest from mold surface) | 404 | 402 | 402 |

The shell may be cured to catalyze polymerization of the material of the shell (e.g., silicone). When the dispersion comprises silicone, for example, curing may crosslink the silicone layers. The curing temperature may range from about 115.0° C. to about 135.0° C., such as from about 120.0° C. to about 130.0° C., from about 122.0° C. to about 128.0° C., from about 125.0° C. to about 130.0° C., or from about 125.0° C. to about 135.0° C. For example, the curing temperature may be 125.0° C.±5.0° C. The curing temperature may be at least 100.0° C., 105.0° C., 110.0° C., 115.0° C. 120.0° C., 125.0° C., 130.0° C., 135.0° C., 140.0° C., or higher. The curing temperature may be at most 140.0° C., 135.0° C., 130.0° C., 125.0° C., 120.0° C., 115.0° C., 110.0° C., 105.0° C., 100.0° C., or less. Curing may be performed for a period of time (or curing time) ranging from about 60 minutes to about 100 minutes, such as from about 70 minutes to about 90 minutes, from about 85 minutes to about 95 minutes, or from about 80 minutes to about 90 minutes. The curing time may be 82.0±5.0 minutes or 85.0±2.0 minutes. The curing time may be at least about 50 minutes, 55 minutes, 60 minutes, 65 minutes, 70 minutes, 75 minutes, 80 minutes, 85 minutes, 90 minutes, 95 minutes, 100 minutes, or longer. In some embodiments, the curing time may be at most about 100 minutes, 95 minutes, 90 minutes, 85 minutes, 80 minutes, 75 minutes, 70 minutes, 65 minutes, 60 minutes, 55 minutes, 50 minutes, or shorter.

The shell may be removed from the mold after curing. The shell may then be inverted, such that the layer farthest from the mold defines the innermost surface of the shell, and the layer formerly in contact with the mold defines the outermost surface of the shell.

In some cases, the mold surface may have a texture, such that the outermost surface of the implant is texturized. For example, the shell may be prepared using a mandrel having a texturized surface, optionally wherein the surface of the mandrel has been texturized using sandblasting with abrasive particles to achieve the desired surface features (a mirror image of the desired peaks, valleys, roughness, kurtosis, density of contact points, etc.). In some examples, the shell may be prepared using a mandrel as described in WO 2017/196973, incorporated by reference herein.

The shell optionally may be inspected for quality, e.g., to identify and discard any shells with defects. In some cases, the thickness of the shell may be measured, for example, at various locations of the shell.

As mentioned above, the implant may comprise a filler, which may be introduced into a cavity formed by the shell, such that the filler partially or completely fills the cavity. In some examples herein, the filler comprises a silicone gel. The silicone gel may be prepared by combining a first mixture and a second mixture. The first mixture may comprise mixture of siloxanes and silicones, dimethyl, and vinyl group-terminated. The second mixture may comprise mixture of siloxanes and silicones, dimethyl, methyl hydrogen, dimethyl, and vinyl group-terminated. To prepare the filter, the first mixture may be mixed with the second mixture in a ratio that provides a suitable gel penetration value, such as between 50-60¹⁄₁₀ mm. In some embodiments, the first mixture and the second mixture may be combined in a weight ratio ranging from about 1:2 to about 2:1, such as in a ratio of about 1:1. In some embodiments, the first mixture and the second mixture may be combined in a weight ratio (first mixture:second mixture) ranging from about 1:4 to about 4:1 (about 0.25 to about 4), such as a weight ratio ranging from about 1:3 to about 3:1 (about 0.33 to about 3), or about 1:2 to about 2:1 (about 0.5 to about 2). For example, the weight ratio of the first mixture to the second mixture may range from about 0.5 to about 2, about 1 to about 3.5, about 2.5 to about 3.5, about 3 to about 3.3, or about 2.8 to about 3.2. In some examples, the first mixture and the second mixture may be combined in a weight ratio (first mixture:second mixture) of at least 1:10, 1:9, 1:8, 1:7, 1:6, 1:5, 1:4, 1:3, 1:2, 1:1, or more. Further, for example, the first mixture and the second mixture may be combined in a weight ratio (first mixture:second mixture) at most about 10:1, 9:1, 8:1, 7:1, 6:1, 5:1, 4:1, 3:1, 2:1, 1:1, or less.

Implants may be assembled by introducing the filler material into the shell, which may occur before or after securing a patch to the shell. In some examples, a patch may be affixed to the shell before introducing a filler material into a cavity defined by the shell. For example, a silicone patch corresponding to the dimensions of an aperture resulting from the molding process may be applied and vulcanized to seal the patch to the shell. Optionally, the shell may be leak-tested to confirm that the patch has been securely attached. The patch then may be cured, e.g., with heat and/or pressure. A suitable filler material, e.g., silicone gel, may be introduced into the shell, such as by injection through the patch. In some examples, the filler may be introduced into the shell to 100% or less the nominal volume defined by the mold (e.g., the head of a mandrel) in order to reach the desired final shape.

Before or after introducing the filler, the process may include introducing a UDI, e.g., a transponder, into the implant. For example, the transponder may be placed inside the shell before affixing the patch to the shell, after affixing the patch to the shell but before injecting a filler, or after injecting a filler into the cavity of the shell. The transponder may be heavier than the filler, such that the transponder falls by gravity to rest against the inner surface of the shell, the transponder being movable through the filler prior to curing of the filler. The implant optionally may be vacuum tested, e.g., to remove air bubbles, and then the implant may be sealed. For example, the filling hole in the patch may be closed with a suitable adhesive, such as a curable, silicone-based adhesive.

Finally, the filler may be cured, e.g., in a gel curing cycle. The implant may be placed in a cavity of a substrate, such as a curing cup having a concave surface for receiving the implant, in order to maintain the symmetrical shape (e.g., symmetry of posterior and anterior apices) during the curing process. In some examples, the substrate may comprise a heat-safe material, such as a ceramic. The implant then may be inspected for quality (to identify and discard implants with defects).

Non-limiting examples of implants according to the present disclosure include the following:

In at least one example, the implant is a round-shaped body contouring implant comprising a silicone shell and silicone gel filler, wherein the shell includes a patch at or proximate a posterior or anterior apex of the shell. The patch may by generally circular in shape and have a diameter of about 25 mm to about 30 mm, such as about 26 mm, about 27 mm, about 28 mm, or about 29 mm. The implant may have three plane of symmetry, e.g., about the xy plane (posterior side symmetric to anterior side), about the xz plane (the left side symmetric to the right side), and about the yz plane (the upper portion symmetric to the lower portion).

In at least one example, the implant is a round-shaped body contouring implant comprising a silicone shell and silicone gel filler, wherein the shell includes a patch at or proximate a posterior or anterior apex of the shell. The patch may by generally circular in shape and have a diameter of about 15 mm to about 25 mm, such as about 16 mm, about 17 mm, about 18 mm, about 19 mm, about 20 mm, about 21 mm, about 22 mm, about 23 mm, or about 24 mm. The implant may have three plane of symmetry, e.g., about the xy plane (posterior side symmetric to anterior side), about the xz plane (the left side symmetric to the right side), and about the yz plane (the upper portion symmetric to the lower portion).

In at least one example, the implant is a round-shaped body contouring implant comprising a silicone shell and silicone gel filler, wherein the shell includes a patch that is not centered at the posterior or anterior apex of the shell.

That is, the patch is located between an apex and the implant equator, e.g., the patch having a shortest distance to the equator of about 3 mm to about 7 mm, such as about 3.5 mm, about 4 mm, about 4.5 mm, about 5 mm, about 5.5 mm, about 6 mm, or about 6.5 mm between the patch and the equator. For example, the patch may by generally circular in shape and have a diameter of about 25 mm to about 30 mm, such as about 26 mm, about 27 mm, about 28 mm, or about 29 mm, or a diameter of about 15 mm to about 25 mm, such as about 16 mm, about 17 mm, about 18 mm, about 19 mm, about 20 mm, about 21 mm, about 22 mm, about 23 mm, or about 24 mm. The implant may have three planes of symmetry, e.g., about the xy plane (posterior side symmetric to anterior side), about the xz plane (the left side symmetric to the right side), and about the yz plane (the upper portion symmetric to the lower portion).

In at least one example, the implant is a round-shaped body contouring implant comprising a silicone shell and silicone gel filler, wherein the shell includes a patch that is not centered at the posterior or anterior apex of the shell. That is, the patch is located between an apex and the implant equator, e.g., the patch having a shortest distance to the equator of about 10 mm to about 40 mm, such as about 15 mm to about 25 mm, e.g., about 18 mm, about 18.5 mm, about 19 mm, about 19.5 mm, about 20 mm, about 20.5 mm, about 21 mm, about 21.5 mm, or about 22 mm between the patch and the equator. For example, the patch may by generally circular in shape and have a diameter of about 25 mm to about 30 mm, such as about 26 mm, about 27 mm, about 28 mm, or about 29 mm, or a diameter of about 15 mm to about 25 mm, such as about 16 mm, about 17 mm, about 18 mm, about 19 mm, about 20 mm, about 21 mm, about 22 mm, about 23 mm, or about 24 mm. The implant may have three planes of symmetry, e.g., about the xy plane (posterior side symmetric to anterior side), about the xz plane (the left side symmetric to the right side), and about the yz plane (the upper portion symmetric to the lower portion).

The following examples are intended to illustrate the present disclosure without, however, being limiting in nature. It is understood that the present disclosure encompasses additional embodiments consistent with the foregoing description and following examples.

EXAMPLES

Example 1

Several implants including four breast implants (A, B, C, and D) and an inflatable tissue dissector (E) were prepared according to Table 2. The penetration value (1/10 mm) of the silicone gel used for breast implants A-D ranged from 10 to 60, wherein higher penetration values correspond to lower viscosity characteristics.

TABLE 2

|  | Shell | Filler | Shape | Plane(s) of Symmetry |
| --- | --- | --- | --- | --- |
| Implant A | Silicone | Silicone gel | Round | xz (left/right) yz (upper/lower) |
| Implant B | Silicone | Silicone gel | Round | xz (left/right) yz (upper/lower) |
| Implant C | Silicone | Silicone gel | Round | xz (left/right) yz (upper/lower) |

TABLE 2-continued

|  | Shell | Filler | Shape | Plane(s) of Symmetry |
| --- | --- | --- | --- | --- |
| Implant D | Silicone | Silicone gel | Round | xz (left/right) yz (upper/lower) xy (posterior/anterior) |
| Implant E | Silicone | Air | Round | xz (left/right) yz (upper/lower) xy (posterior/anterior) |

Figure 5:
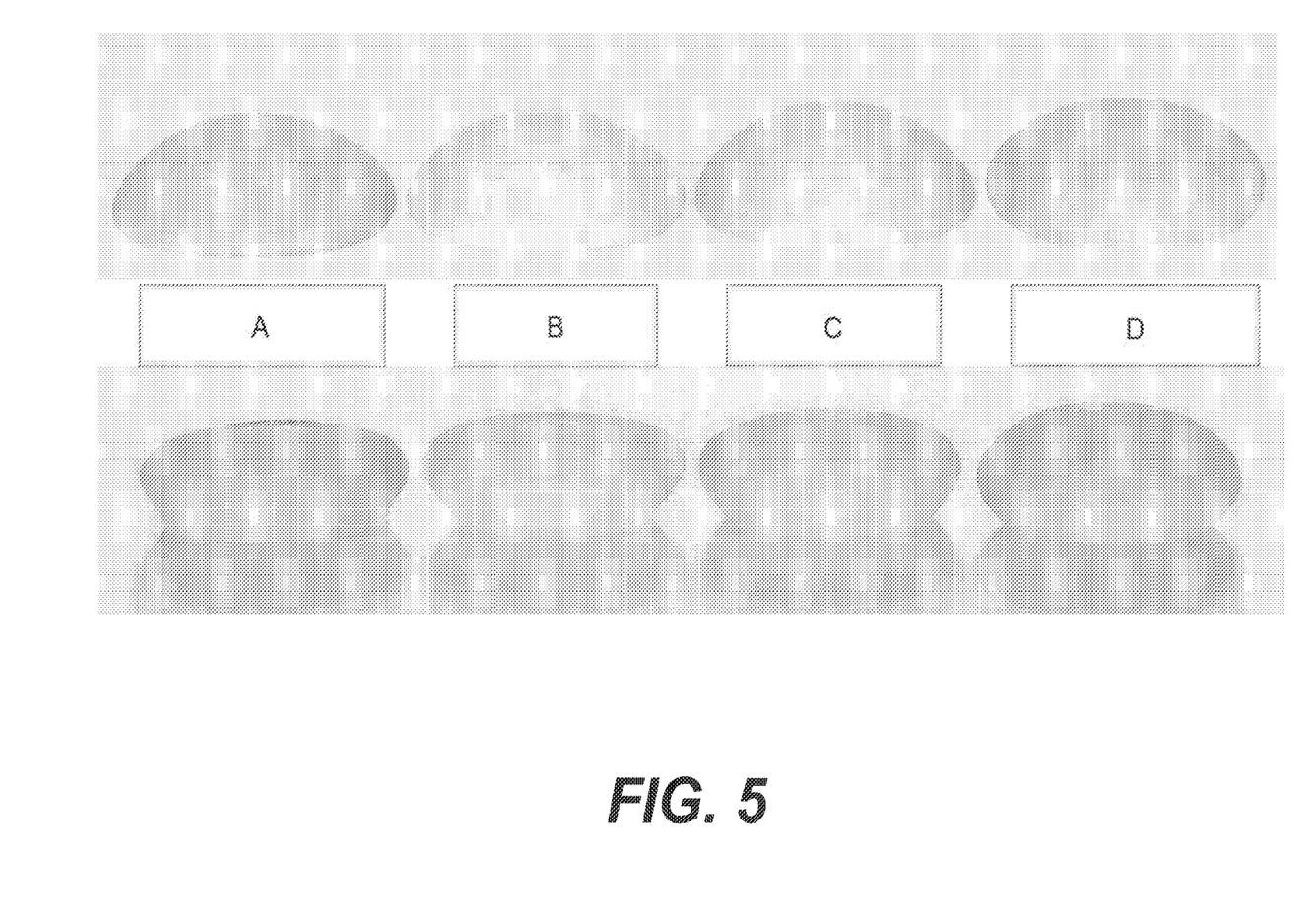
FIG. 5 shows different implants discussed in Example 1.

Photographs of breast implants A-D (side views) are shown in FIG. 5. Implants A-C had flat posterior surfaces and lacked symmetry about the xy plane (about their equators). In comparison, implant D according to the present disclosure had symmetric posterior and anterior surfaces. The viscosity of the silicone gel used for implant D allowed for the gel to respond to gravity and maintain symmetry provided by the shape of the implant shell.

Any aspect or feature in any embodiment may be used with any other embodiment set forth herein. It will be apparent to those skilled in the art that various modifications and variations can be made in the disclosed implants, implant features, and processes without departing from the scope of the disclosure. Other embodiments will be apparent to those skilled in the art from consideration of the specification and practice of the disclosure disclosed herein. It is intended that the specification and examples be considered as exemplary only.

What is claimed is:

1. A breast implant formed from a biocompatible material, the breast implant comprising:
   an anterior side extending from a first end to a second end and having a first arc-shaped profile, the first arc-shaped profile defining a first projection with a first apex;
   a posterior side extending from a first end to a second end and having a second arc-shaped profile, the second arc-shaped profile defining a second projection similar to the first projection with a second apex; and
   a dividing plane corresponding to an equator of the breast implant separating the anterior side from the posterior side;
   wherein the first apex is closer to the first end of the anterior side than the second end of the anterior side and the second apex is closer to the first end of the posterior side than the second end of the posterior side;
   wherein the anterior side and posterior side form a shell, the shell including:
      at least one first layer formed from at least one first material; and
      a second layer arranged as an innermost layer of the shell formed from a second material;
      wherein the at least one first material is different from the second material.

2. The breast implant of claim 1, wherein the first apex of the first projection is closer to a midpoint between the first end and the second end than to the first end of the anterior side and the second apex of the second projection is closer to the midpoint than the first end of the posterior side.

3. The breast implant of claim 1, wherein an apex axis passes through the first apex and the second apex and the apex axis is generally perpendicular to the dividing plane.

4. The breast implant of claim 1, wherein the dividing plane is generally equidistant from the first apex and the second apex.

5. The breast implant of claim 1, wherein the breast implant has a rounded shape.

6. The breast implant of claim 1, wherein the breast implant has an oval shape.

7. The breast implant of claim 1, wherein the breast implant has a teardrop shape.

8. A breast implant comprising:
a shell defining an interior cavity and including a first end longitudinally spaced from a second end, a posterior side having a first curved profile, and an anterior side having a second curved profile, the posterior side and anterior side are separated by a plane extending between the first end and the second end;
wherein the shell has at least two planes of symmetry;
wherein the shell has at least a first layer and a second layer, the second layer is different from the first layer and the second layer comprises a low diffusion barrier material; and
a filler material disposed within the interior cavity of the shell.

9. The breast implant of claim 8, wherein the second layer is an innermost layer of the shell and is in contact with the filler material and comprises the low diffusion barrier material.

10. The breast implant of claim 8, wherein a first apex of the first curved profile is generally aligned with a second apex of the second curved profile.

11. A breast implant comprising:
a shell formed from a biocompatible material and defining an interior cavity, the shell including:
a plurality of layers including at least a first plurality of layers and a second plurality of layers;
wherein the first plurality of layers is a different material than the second plurality of layers;
a posterior side having a first rounded profile;
an anterior side having a second rounded profile;
an upper side; and
a lower side;
wherein a first end of the posterior side and a first end of the anterior side meet at a first point at one of the upper side or the lower side, and a second end of the posterior side and a second end of the anterior side meet at a second point at the other of the upper side or the lower side;
wherein a plane connecting the first point and the second point includes an equator of the shell; and
a filler material disposed within the interior cavity.

12. The breast implant of claim 11, wherein the filler material comprises a silicone material.

13. The breast implant of claim 12, wherein the silicone material comprises a silicone gel.

14. The breast implant of claim 11, wherein the posterior side and the anterior side are symmetrical about the equator of the shell.

15. The breast implant of claim 11, wherein the biocompatible material of the second plurality of layers comprises a low diffusion barrier material.

16. The breast implant of claim 15, wherein the second plurality of layers is an innermost layer of the shell.

17. The breast implant of claim 16, wherein the second plurality of layers is in contact with the filler material disposed within the interior cavity.

* * * * *